United States Patent
Ji et al.

(10) Patent No.: US 9,389,442 B2
(45) Date of Patent: Jul. 12, 2016

(54) ARRAY SUBSTRATE, DETECTING METHOD AND DETECTING APPARATUS THEREOF

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Xinyou Ji, Beijing (CN); Jian Guo, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 0 days.

(21) Appl. No.: 14/395,597

(22) PCT Filed: Apr. 10, 2013

(86) PCT No.: PCT/CN2013/074033
§ 371 (c)(1),
(2) Date: Oct. 20, 2014

(87) PCT Pub. No.: WO2014/121555
PCT Pub. Date: Aug. 14, 2014

(65) Prior Publication Data
US 2015/0077753 A1    Mar. 19, 2015

(30) Foreign Application Priority Data
Feb. 5, 2013 (CN) .......................... 2013 1 0046771

(51) Int. Cl.
*G02F 1/13* (2006.01)
*G01R 31/02* (2006.01)
(Continued)

(52) U.S. Cl.
CPC ............ *G02F 1/1309* (2013.01); *G01N 21/958* (2013.01); *G01R 31/02* (2013.01);
(Continued)

(58) Field of Classification Search
CPC ................. G01N 2021/9513; G01N 21/958; G01R 31/02; G02F 1/1309; G02F 1/136259; G02F 1/13624; G02F 1/136213; G02F 2001/136263
USPC ........ 356/300–334, 402–425; 349/42, 43, 44, 349/92, 54, 192; 116/208; 257/E29.276
See application file for complete search history.

(56) References Cited

U.S. PATENT DOCUMENTS 5,303,574 A * 4/1994 Matossian et al. .................. 73/7
5,745,229 A * 4/1998 Jung et al. ........................ 356/73
(Continued)

FOREIGN PATENT DOCUMENTS

CN          1797016 A  *  7/2006

OTHER PUBLICATIONS

English Machine Translation of CN 1797016A, EPO Patent Translate, Jun. 6, 2015, 8 pages.*
Written Opinion of the International Searching Authority dated Jan. 11, 2013; PCT/CN2013/074033.

*Primary Examiner* — Michael A Lyons
*Assistant Examiner* — Dominic J Bologna
(74) *Attorney, Agent, or Firm* — Ladas & Parry LLP

(57) ABSTRACT

The present disclosure provides an array substrate comprising a structure to be detected disposed on a base substrate. An additional layer for detecting the structure to be detected is broken is disposed below the structure to be detected. The additional layer has a color different from that of the structure to be detected and a same pattern shape as that of the structure to be detected. The present disclosure also provides a detecting method and detecting apparatus of the array substrate described above. According to the array substrate, the detecting method and the detecting apparatus of the present disclosure, an early detection of the breakage defect occurred during the fabrication process of the array substrate can be achieved so as to discover and eliminate those defects as early as possible, which improves throughput and yield.

18 Claims, 2 Drawing Sheets

(51) Int. Cl.
*G09G 3/00* (2006.01)
*G01N 21/958* (2006.01)
*G02F 1/1362* (2006.01)
*G01N 21/95* (2006.01)

(52) U.S. Cl.
CPC ......... *G02F1/136259* (2013.01); *G09G 3/006* (2013.01); *G01N 2021/9513* (2013.01); *G01N 2201/062* (2013.01); *G02F 2001/136254* (2013.01); *G02F 2001/136268* (2013.01); *H01L 2225/06596* (2013.01)

(56) References Cited

U.S. PATENT DOCUMENTS

| | | | | |
|---|---|---|---|---|
| 6,288,765 | B1* | 9/2001 | Tanaka | G02F 1/1339 349/153 |
| 7,739,974 | B1* | 6/2010 | Anderson | C09D 5/1693 114/222 |
| 2002/0044229 | A1* | 4/2002 | Kim | 349/43 |
| 2011/0141376 | A1* | 6/2011 | Tsubata | G02F 1/136213 348/731 |

* cited by examiner

ARRAY SUBSTRATE, DETECTING METHOD AND DETECTING APPARATUS THEREOF

TECHNICAL FIELD

The disclosure relates to a display technology field; in particular, relates to an array substrate, a detecting method and a detecting apparatus thereof.

BACKGROUND

Thin film transistor liquid crystal display (TFT-LCD) dominates current flat screen display market due to characteristics such as small volume, low power consumption and no radiation and so on. TFT-LCD is formed by cell assembling an array substrate and a color filter substrate. In the array substrate, gate scanning lines and data signal lines are arranged to cross each other to define pixel regions, and pixel electrodes and the thin film transistors are arranged in respective pixel regions.

Bright lines and bright spots are major defects occurred during current TFT-LCD fabricating process. The bright lines are presented as lines with bright colors on the display panel which do not vary with the color change on the screen. The bright lines are caused largely by the breakage of the gate scanning lines or data signal lines due to the dusts. The bright spots are caused by various reasons such as dusts, thin film residues etc. For 4 mask technology, the two major defects are gray tone bridging and channel breakage which are bright spots defects caused by a-Si under-etch and a-Si over-etch respectively in the channel region. It is difficult to detect these two kinds of defects during fabricating process. The gray tone bridging can not be detected until a testing stage of the array substrate; whereas the channel breakage can not even be detected during the testing stage of the array substrate, if the channel is not completely broken and the charging and discharging function can still work. In this case, it can only be detected, evident as a mura later in a testing stage of the liquid crystal cell.

In view of the above, all the above defects can only be detected in the testing stage of array substrate at earliest, and some channel breakage defects can not be detected until the testing stage of the liquid crystal cell. This could cause a delay in adjusting the apparatus, so that similar defects would continue to occur in a large batch of products.

SUMMARY

In view of the above, the present disclosure provides an array substrate, a detecting method and a detecting apparatus thereof, such that an early detection of the breakage defect occurred during the fabrication process of the array substrate can be achieved so as to discover and eliminate those defects as early as possible, which improves throughput and yield.

According to one aspect of the present disclosure, an array substrate is provided. The array substrate comprises a structure to be detected disposed on a base substrate. An additional layer for detecting whether the structure to be detected is broken is disposed below the structure to be detected. The additional layer has a color different from that of the structure to be detected and a same pattern shape as that of the structure to be detected.

The structure to be detected is at least one of following structures: a gate, a gate scanning line, a data signal line, an active layer, a source, and a drain.

A transparent protective layer is disposed above the additional layer.

The additional layer is one of a copper layer, an oxide layer of silicon, a nitride layer of silicon, and polyimide layer with addition of a colorant.

Both the additional layer and the transparent protective layer have a thickness of no more than 5000 Å.

According to another aspect of the present disclosure, a detecting method of the array substrate described as above is provided. The method comprises: irradiating white lights on the array substrate formed with the additional layer; and determining a color of reflection lights reflected by the array substrate. If the color of the reflection lights has the color of the additional layer, then the structure to be detected corresponding to the color of the additional layer is determined to have a breakage defect. If the color of the reflection lights has no color of the additional layer, then the structure to be detected corresponding to the color of the additional layer is determined to have no breakage defect.

At the step of determining the color of the reflection lights, a light filter unit with the same color as that of the additional layer is disposed in a light path of the reflection lights, and the color of the reflection lights reflected by the array substrate is determined by the lights passing through the light filter unit.

According to another aspect of the present disclosure, a detecting apparatus of the array substrate described as above is provided. The apparatus comprises: a detecting stage for placing the array substrate to be detected thereon; a light source of white color for irradiating white lights on the array substrate formed with the additional layer; and a light filter unit for filtering the lights with colors different from the color of the additional layer.

The light filter unit is a light filter with the same color as that of the additional layer.

The detecting apparatus further comprises a light detecting unit for identifying the same color as that of the additional layer.

The detecting apparatus further comprises a housing. The light source and the light filter unit are disposed above the detecting stage on opposing sides of the detecting stage respectively, and the light detecting unit is disposed above the light filter unit, and the housing is disposed outside so as to accommodate the detecting stage, the light source, the light filter unit and the light detecting unit.

In summary, by forming the additional layer with a color different form that of the structure to be detected in the array substrate and detecting the color of the reflection lights reflected by the array substrate, an early detection of the breakage defects in the pattern of the array substrate can be achieved, so that such defects in the array substrate can be discovered in time to enable the adjustment of the apparatus as early as possible, which reduces the occurrence of defected products.

BRIEF DESCRIPTION OF THE DRAWINGS

For illustrating the technical solutions of the present disclosure or the prior arts more clearly, accompanying drawings used in the description of the technical solutions according to the present disclosure and the prior arts will be introduced briefly. It is apparent that the accompanying drawings in the description as following are only for describing a part of the embodiments of the present disclosure. The skilled in the art can obtain other drawings based on these accompanying drawings without creative works.

DESCRIPTION OF REFERENCE NUMBERS

Figure 1:
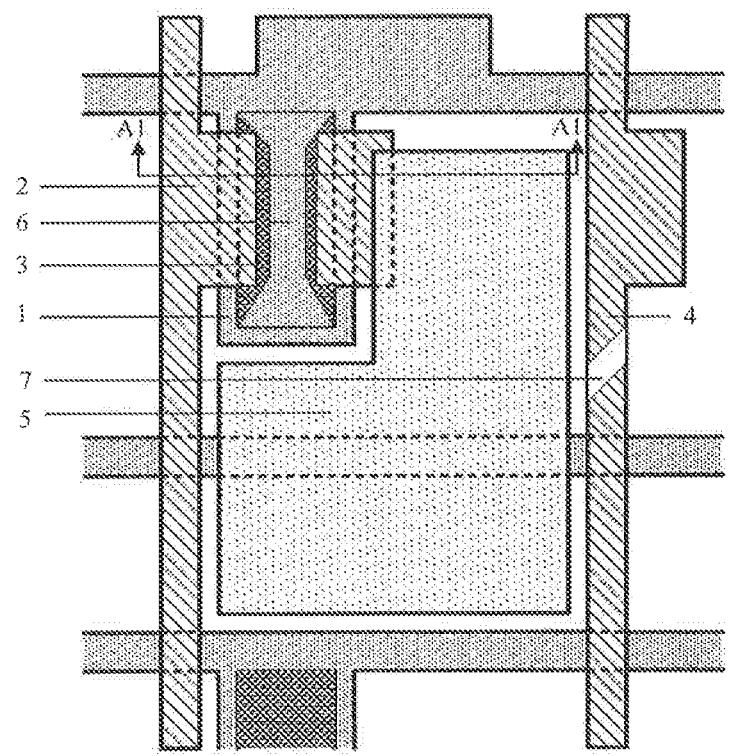
FIG. 1 is schematic plan view showing channel breakage defects in the array substrate.

1 gate; 2 source/drain; 3 active layer; 4 data signal one; 5 pixel electrode; 6 breakage defect of active layer below channel; 7 data signal line breakage defect; 8 substrate; 9 gate insulating layer; 10 passivation layer; 11 second additional layer; 12 second transparent protective layer; 13 detecting stage; 14 array substrate; 15 light source; 16 light filter unit; 17 light detecting unit; 18 housing.

DETAILED DESCRIPTION

The technical solutions according to embodiments of the present disclosure will be described clearly and completely below with respect to drawings of embodiments of the present invention. It is understood that the described embodiments are only a part of but not all of embodiments of the present disclosure. Based on the described embodiments of the present disclosure, all other embodiments obtained by those of ordinary skilled in the art without any creative labor fall into the protective scope of the present disclosure.

Unless defined otherwise, the technical term or scientific term used herein should have the common meaning understood by the skilled in the art pertaining to the present disclosure. The phrases such as "first", "second" and the like used in the description and claims of the present disclosure do not indicate any order, quantity or degree of importance, but only for purpose of differentiating different components. Similarly, the articles such as "a" or "an" do not indicate the number limitation of numbers, and only indicates the existence of at least one. The phrases such as "connection" or "connecting" are not limited to physical or mechanical connection, but can also include electrical connection, no matter directly or indirectly. The phrases such as "above", "below", "left", "right" are only used to indicate relative positional relationship so that if the absolute position of the described object is changed, the relative positional relationship is also changed correspondingly.

The present disclosure provides an array substrate. The array substrate comprises a structure to be detected disposed on a base substrate. An additional layer for detecting whether the structure to be detected is broken is disposed below the structure to be detected. The additional layer has a color different from that of the structure to be detected and a same pattern shape as that of the structure to be detected. Therefore, an early detection of the breakage defect occurred during the fabrication process of the array substrate can be achieved so as to discover and eliminate those defects as early as possible, which improves throughput and yield.

The structure to be detected is at least one of following structures: a gate, a gate scanning line, a data signal line, an active layer, a source, and a drain.

A transparent protective layer for protecting the additional layer is disposed above the additional layer. The transparent protective layer can be a typical transparent protective material such as a same material for the gate insulating layer in the array substrate, preferably a silicon nitride (SiNx).

The additional layer can be one of a copper layer, an oxide layer of silicon, a nitride layer of silicon, and polyimide layer with addition of a colorant, but the additional layer is limited thereto, as long as the additional layer has the same color as that of the structure to be detected located thereabove.

The additional layer and transparent protective layer can be as thin as possible in order to prevent an increase in the pixel capacitance and induce change in the stress of the substrate. Both the additional layer and the transparent protective layer have a thickness of no more than 5000 Å, preferably in a range of 10 Å-3000 Å.

The present disclosure provided a detecting method of the array substrate described as above. The method comprises: irradiating white lights on the array substrate formed with the additional layer; and determining a color of reflection lights reflected by the array substrate. If the color of the reflection lights has the color of the additional layer, then the structure to be detected corresponding to the color of the additional layer is determined to have a breakage defect. If the color of the reflection lights has no color of the additional layer, then the structure to be detected corresponding to the color of the additional layer is determined to have no breakage defect.

At the step of determining the color of the reflection lights, a light filter unit with the same color as that of the additional layer is disposed in a light path of the reflection lights, and the color of the reflection lights reflected by the array substrate is determined by the lights passing through the light filter unit.

The present disclosure also provides a detecting apparatus of the array substrate described as above. The apparatus comprises: a detecting stage for placing the array substrate to be detected thereon; a light source of white color for irradiating white lights on the array substrate formed with the additional layer; and a light filter unit for filtering the lights with colors different from the color of the additional layer.

The light filter unit is a light filter with the same color as that of the additional layer.

The detecting apparatus further comprises a light detecting unit for identifying the same color as that of the additional layer.

In addition, the light source and the light filter unit are disposed above the detecting stage on opposing sides of the detecting stage respectively, and the light detecting unit is disposed above the light filter unit.

The present disclosure will be described in more detail by reference to the following embodiments of respective structure to be detected. It is understood that a respective structure to be detected is illustrated as an example in each embodiment of the present disclosure, and a transparent protective layer is preferably disposed above the additional layer. It is understood that the embodiments of the present disclosure can be combined in any way possible.

First Embodiment

The structure to be detected in the present embodiment of the disclosure is a data signal line.

As shown in FIG. 1, in the array substrate, gate scanning lines are configured to apply ON voltage to each row of the gates in displaying each frame. After turn on the selected row, data signal line executes a writing operation of the electrical signals to the selected row of the pixels. The electrical signals are transferred to the pixel electrodes 5 via the drain electrode after passing through an active layer 3 below the channel.

When the data signal line suffers data signal line breakage defects 7 due to dust and the like, the data signal lines is broken at corresponding portion, the electrical signals cannot be applied to the respective pixel electrode, and the liquid crystal molecules cannot be rotated by the pixel electrode. Therefore, in a normal white mode, the lights will be always transmitted through the pixels of the defected portion, resulting in bright line defects.

In this case, a first additional layer is disposed below the data signal line, primarily as a marker for the defect. The first additional layer has a color different from that of the data signal line and a shape and pattern the same as that of the data signal line. The data signal line is typically made of a material with stable chemical property and relative high resistivity such as metals of Ta, Cr, Mo or the alloy thereof, or a low resistivity metal Cu. If the data signal line is made of Mo, the structure to be detected has a black color, the first additional layer can be a polyimide layer with red colorant. The data signal lines can be made of other materials, as long as the first additional layer has a color different from that of the structure to be detected and such material will not be illustrate exhaustively herein.

In a detecting method of the array substrate according to the present embodiment, white lights are irradiated on the array substrate formed with the first additional layer; and the array substrate formed with the first additional layer has not only the structure of the data signal line, but also the structures of gate scanning lines, gate electrodes, source or drain electrodes and so on. But there can be no other structure disposed above the data signal lines, otherwise it will affect the determination of the breakage defects. A color of reflection lights reflected by the array substrate is determined. If the color of the reflection lights is red, then the structure above the first additional layer is determined to have a breakage defect. If the color of the reflection lights is not a red color, then the structure above the first additional layer is determined to have no breakage defect. At the step of determining the color of the reflection lights, a light filter unit with the same color as that of the first additional layer is disposed in a light path of the reflection lights, and the color of the reflection lights reflected by the array substrate is determined by the lights passing through the light filter unit.

A detecting apparatus of the array substrate according to the present embodiment comprises: a detecting stage for placing the array substrate to be detected thereon; a light source of white color for irradiating white lights on the array substrate formed with the additional layer; and a light filter unit for filtering the lights with colors different from the color of the additional layer. The light filter unit is a light filter with the same color as that of the additional layer. In the present embodiment, the light filter unit is a red light filter for absorbing lights other than the red light and only allowing red lights passing therethrough.

The detecting apparatus further comprises a light detecting unit for identifying the same color as that of the additional layer. The light detecting unit can detect qualitatively or quantitatively in a principle that only red lights can pass through the red light filter unit. If the structure above the additional layer has a breakage defect, the light detecting unit can only identify red color after white lights are irradiated onto the polyimide layer with the red colorant and pass through the red light filter. If the structure above the additional layer does not have a breakage defect, the light detecting unit can not identify red color or only traces of red color (in such case, a quantitative detection unit can be added in the light detection unit in order to determine the occurrence of the breakage defect more accurately), after white lights are irradiated onto the black data signal line and pass through the red light filter.

In addition, the light source and the light filter unit are disposed above the detecting stage on opposing sides of the detecting stage respectively, and the light detecting unit is disposed above the light filter unit. When the white lights are irradiated on the array substrate to be reflected, the lights can reach the light detection unit via the light filter unit. This apparatus has a simple structure and can detect the occurrence of breakage defects of the structure to be detected readily and quickly.

Second Embodiment

The structure to be detected in the present embodiment of the disclosure is one of an active layer, a source or drain electrode, a data signal line.

Figure 2:
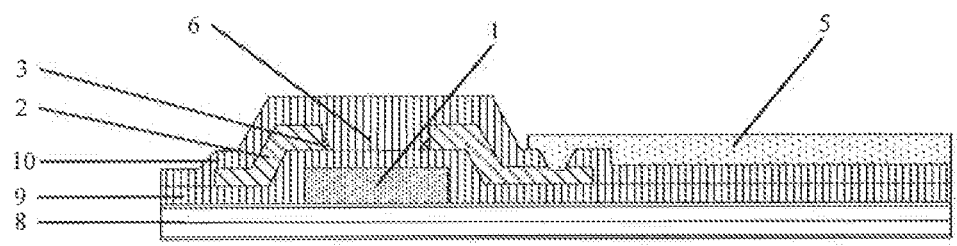
FIG. 2 is a schematic sectional view taken along A1-A1 line in the FIG. 1.
Figure 3:
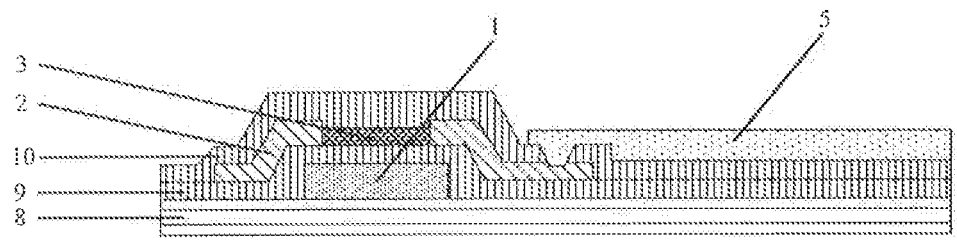
FIG. 3 is a schematic sectional view of a normal array structure corresponding to FIG. 2.

As shown in FIG. 2 and FIG. 3, a breakage defect 6 is caused by an over-etch of the active layer 3 below the channel. In this case, the active layer 3 below the channel is partially etched off and a gate insulating layer 9 is exposed; therefore the defected pixel has a charging/discharging function different from that of a normal pixel. The ON current Ion, off current Ioff and threshold voltage Vth can vary to form bright spots defect or mura defects. Such defects can usually be found out until the testing stage, and can not be detected immediately after the respective process in order to find a proper solution, which delay the timing of correction so that the defects are more difficult to repair or even impossible to repair.

In this case, a second additional layer is disposed below the active layer and between the gate insulating layer and the active layer, primarily as a marker for the defect. The second additional layer has a color different from that of the active layer and a shape and pattern the same as that of the active layer. The active layer is typically made of a-Si or oxide semiconductor such as IGZO (indium gallium zinc oxide). If the active layer is made of a-Si, the structure to be detected has a reddish brown color, the second additional layer can be a polyimide layer with green colorant. The active layer can be made of other materials, as long as the second additional layer has a color different from that of the structure to be detected, and such material will not be illustrate exhaustively herein.

In a detecting method of the array substrate according to the present embodiment, white lights are irradiated on the array substrate formed with the second additional layer; and the array substrate formed with the second additional layer has not only the structure of the active layer, but also the structures of gate scanning lines, gate electrodes, source and drain electrodes and so on. But there can be no other structure disposed above the active layer, otherwise it will affect the determination of the breakage defects. A color of reflection lights reflected by the array substrate is determined. If the color of the reflection lights is green, then the structure above the second additional layer is determined to have a breakage defect. If the color of the reflection lights is not a green color, then the structure above the second additional layer is determined to have no breakage defect. At the step of determining the color of the reflection lights, a light filter unit with the same color as that of the first additional layer is disposed in a light path of the reflection lights, and the color of the reflection lights reflected by the array substrate is determined by the lights passing through the light filter unit.

A detecting apparatus of the array substrate according to the present embodiment comprises: a detecting stage for placing the array substrate to be detected thereon; a light source of white color for irradiating white lights on the array substrate formed with the additional layer; and a light filter unit for filtering the lights with colors different from the color of the additional layer. The light filter unit is a light filter with the same color as that of the additional layer. In the present embodiment, the light filter unit is a green light filter for absorbing lights other than the green light and only allowing green lights passing therethrough.

The detecting apparatus further comprises a light detecting unit for identifying the same color as that of the additional layer. The light detecting unit can detect qualitatively or quantitatively in a principle that only green lights can pass through the green light filter unit. If the structure above the additional layer has a breakage defect, the light detecting unit can only identify green color after white lights are irradiated onto the polyimide layer with the green colorant and pass through the green light filter. If the structure above the additional layer does not have a breakage defect, the light detecting unit can not identify green color or only traces of green color (in such case, a quantitative detection unit can be added in the light detection unit in order to determine the occurrence of the breakage defect more accurately), after white lights are irradiated onto the reddish brown active layer and pass through the red light filter.

In addition, the light source and the light filter unit are disposed above the detecting stage on opposing sides of the detecting stage respectively, and the light detecting unit is disposed above the light filter unit. When the white lights are irradiated on the array substrate to be reflected, the lights can reach the light detection unit via the light filter unit. This apparatus has a simple structure and can detect the occurrence of breakage defects of the structure to be detected readily and quickly.

Figure 4:
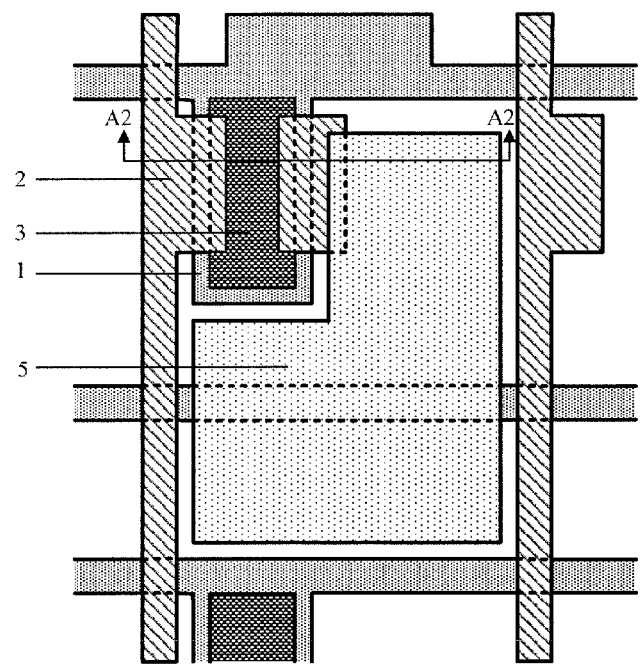
FIG. 4 is schematic plan view of an array substrate structure with the second additional layer according to the second embodiment of the present disclosure.
Figure 5:
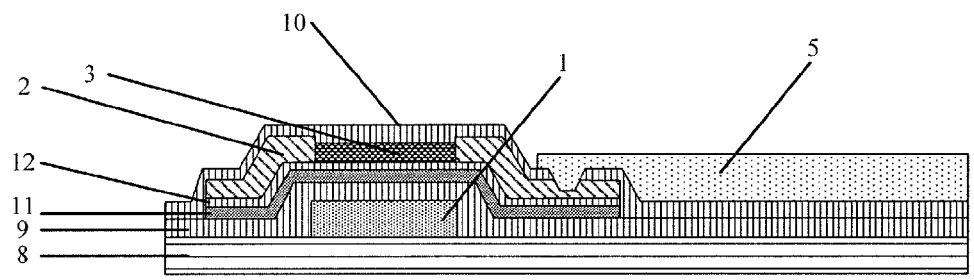
FIG. 5 is schematic sectional view taken along line A2-A2 in the FIG. 4.

FIG. 4 is a plan view of a pixel unit of the array substrate according to the second embodiment of the present disclosure, and FIG. 5 is a schematic sectional view taken along line A2-A2 of FIG. 4. As shown in FIG. 4 and FIG. 5, the array substrate according to the present disclosure comprises a base substrate 8, and a gate scanning line and gate 1, a gate insulating layer 9, a second additional layer 11, a second transparent protective layer 12, a source/drain electrode 2, an active layer 3 below the channel region, a passivation layer 10 and a pixel electrode 5 formed on the base substrate 8 sequentially.

The base substrate can be a typical substrate in the art, such as a glass substrate or a plastic substrate with good transparency and good stability.

The second additional layer 11 serves primarily as a marker for the defect and can be made of a material with a color different from that of the active layer and enduring the temperature in the subsequent processes of the array substrate.

For example, the material of the second additional layer 11 can be a metal such as copper, an insulator such as silicon oxide, silicon nitride, or polymer material such as polyimide resin with colorants.

The second additional layer 11 can be formed by a typical thin film forming method in the art based on the used material. For example, if the second additional layer 11 is a metal layer, such layer can be formed by magnetron sputtering method; if the second additional layer 11 is a polymer material layer, such layer can be formed by methods such as spin coating, printing, ink-jet, etc.; if the second additional layer 11 is an insulating layer, such layer can be formed by deposition. The above material layer can be patterned by either etching or exposing and developing method.

Optionally, a second transparent protective layer 12 is formed on the second additional layer 11. The second transparent protective layer 12 can be formed of a typical transparent protective layer material such as a material the same as that of the gate insulating layer 9, preferably silicon nitride (SiNx) by a typical thin film forming method in the art such as a deposition method.

The second additional layer 11 and second transparent layer 12 formed by the above method has the same shape and pattern as that of the active layer below the channel region.

The second additional layer 11 and second transparent protective layer 12 can be as thin as possible in order to prevent the increase in the pixel capacitance and the stress change of the substrate. The second additional layer 11 and the second transparent protective layer 12 have a thickness of no more than 5000 Å, preferably in a range of 10 Å to 3000 Å.

In addition, if the second additional layer 11 is a silicon oxide or a silicon nitride layer for preventing the etching of silicon, the second transparent protective layer 12 can be omitted, that is, the active layer, the source and drain electrode can be formed directly on the second additional layer 11.

The structure to be detected in the present embodiment can be the active layer and the data signal lines. In this case, the color of the additional layer can be different from the colors of the active layer and the data signal lines. The details will not be repeated due to the same principle.

The structure to be detected in the present embodiment can be the source/drain electrode and the active layer. In this case, the color of the additional layer can be different from the colors of the source/drain electrode and the active layer. The details will not be repeated due to the same principle.

The structure to be detected in the present embodiment can be the source/drain electrode. In this case, the color of the additional layer can be different from the color of the source/drain electrode. The details will not be repeated due to the same principle.

The structure to be detected in the present embodiment can be any combination of the active layer, the source/drain electrode and the data signal lines. The details will not be repeated due to the same principle.

Third Embodiment

The structure to be detected in the present embodiment of the disclosure is at least one of the gate electrode and the gate scanning line.

In the array substrate of the present disclosure, a third additional layer can be formed between the gate electrode 1 and the base substrate 8 and a third transparent layer (not shown) can be formed directly on the third additional layer. The gate electrode and the gate scanning line can be made of a metal material of Cr, W, Cu, Ti, Ta, Mo or an alloy thereof, a multilayer of metals. The third additional layer and the third transparent layer have shapes and patterns the same as that of the gate electrode and/or the gate scanning line and are formed by the same methods and materials as those with respect to the second additional layer and the second transparent layer.

Similarly, if the gate electrode 1 has a breakage defect, the third transparent protective layer therebelow such as SiNx layer and the third additional layer can be exposed to display a corresponding color.

The above embodiments are described in a device operated in TN mode as an example, but the structure related to the additional layer can also be applied to the device operated in ADS mode. ADS mode is a core technology of in-plane electric field and wide viewing angle, which can be described essentially as following. A multi-dimensional electric field can be formed by an electric field generated by the edges of slit electrodes within a same plane and an electric field generated between the slit electrodes and the plate electrodes, so that liquid crystal molecules in all orientations can be rotated between the slit electrodes and on the electrodes within the liquid crystal cell, thereby the operating efficiency of the liquid crystal is improved and light throughput can be increased. The switching technology of the ADS mode can improve the image quality of the TFT-LCD product with advantages such as high resolution, high light throughput, low power consumption, wide viewing angle, high aperture ratio, low aberration and no push Mura, etc. The modifications of the ADS technology include high light throughput I-IDS, high aperture ratio H-ADS and high resolution S-ADS technology and so on for different applications.

Fourth Embodiment

Figure 6:
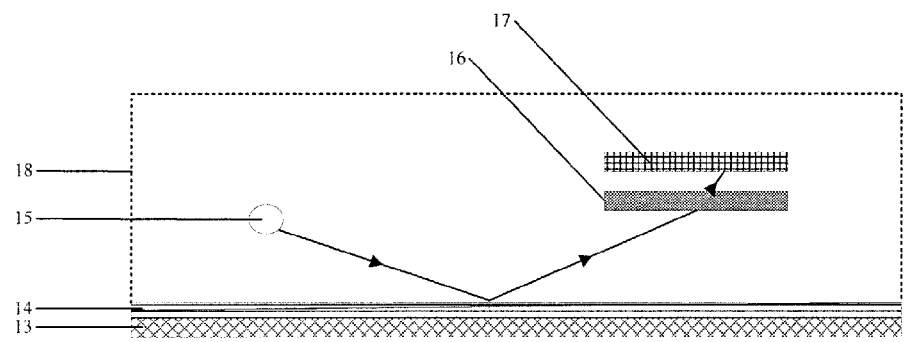
FIG. 6 is a schematic view showing a detecting device for detecting broken defects in the array substrate.

Referring to FIG. 6, a detecting apparatus of the array substrate according to the present embodiment comprises: a detecting stage 13; a light source 15 of white color; a light filter unit 16, a light detection unit 17 and a housing 18. The light source 15 and the light filter unit 16 are disposed above the detecting stage 13 on opposing sides of the detecting stage 13 respectively, and the light detecting unit 17 is disposed above the light filter unit 16. The housing 18 is placed outside of the whole detecting apparatus to accommodate the detecting apparatus.

The light filter unit 16 is for filtering the lights with colors different from the color of the additional layer. The white lights emitted by the light source 15 are reflected by the array substrate 13 placed on the detecting stage 13, and reach the light detecting unit 17 after passing the light filter unit 16. The light detecting unit 17 is for identifying the same color as that of the additional layer.

Furthermore, the testing stage 13 can be made of a material with a color such as black or a material such as marble which can absorb lights emitted from the light source 15, in order to prevent stray lights from affecting the testing result. The light source 15 can be any light sources which can emit white lights, preferably LED with good directivity. The light filter unit 16 is a light filter with the same color as that of the additional layer. The housing 18 can be any opaque material so that a black box enclosing the interior of the apparatus in order to facilitate the determination of the color of the filtered lights.

Fifth Embodiment

The embodiment of the present disclosure provides a detecting method of the array substrate. The method comprises: irradiating white lights on the array substrate formed with the additional layer; and determining a color of reflection lights reflected by the array substrate. If the color of the reflection lights having the color of the additional layer, then the structure above the additional layer is determined to have a breakage defect. If the color of the reflection lights is not the color of the additional layer or contains only traces of the color of the additional layer, then the structure above the additional layer is determined to have no breakage defect. The determination can be performed by human eye or a light detection unit.

At the step of determining the color of the reflection lights, a light filter unit with the same color as that of the additional layer is disposed in a light path of the reflection lights, and the color of the reflection lights reflected by the array substrate is determined by the lights passing through the light filter unit.

In particular, in the apparatus shown in FIG. 6, the array substrate 14 is placed on the testing stage 13. The testing stage is for example a black marble stage. The position of the light source 15 (LED light source) is adjusted so that the white lights emitted by the LED light source 15 are reflected to the light filter unit 16 by the array substrate 14, and reach the light detecting unit 17 after filtering. If the color detected by the light detecting unit 17 is the same as the color of the additional layer, the respective structure to be detected in the array substrate 14 has a breakage defect. If the color detected by the light detecting unit 17 is not the color of the additional layer or contains only traces of the color of the additional layer, then the structure above the additional layer is determined to have no breakage defect.

Typically during the fabricating process of the array substrate, the breakage defects in the active layer below the channel occur in aggregation and rarely distributed in other regions; therefore the lights reflected from a certain region and received by the light detecting unit 1.

Alternatively, a test operator can use tools such as wear glasses with light filters (equivalent to the light filter unit 16) to observe the lights reflected by the array substrate 14 upon irradiating the array substrate 14 placed on the testing stage 13. Such glasses can only transmit the lights with a color the same as that of the additional layer. In this way, the position of the defects occurred in the array substrate can be detected more conveniently, which allow saving detecting time compared with the detecting method described as above.

The present disclosure provides a detecting method of the breakage defects in the array substrate and corresponding detecting apparatus and an array substrate, which achieve an early detection of the breakage defects in the array substrate, so that such defects in the array substrate can be discovered in time when they occur during fabricating process and the fabricating apparatus can be adjusted in time to eliminate the causes for the defects, which resolves the issue in the adjustment delay of the apparatus and reduces the occurrence of defected products in time, thus improving throughput and yield of the product.

The array substrate according to the embodiments of the disclosure can be applied to display devices such as a liquid crystal display panel, a liquid crystal TV, a liquid crystal monitor, a electronic paper, a digital frame, cell phones, and organic light emitting diode display devices and so on.

It should be noted that the above embodiments are only for describing the present disclosure rather than limiting it. Those ordinary skills in the can make various modifications and variant without departing the spirit and the scope of the present disclosure. Therefore all equivalent technical solutions belong to the scope of the present disclosure which is defined by the attached claims.

The invention claimed is:

1. An array substrate, comprising: a structure to be detected disposed on a base substrate, wherein an additional layer for detecting whether the structure to be detected is broken is disposed below the structure to be detected, wherein the additional layer has a color different from that of the structure to be detected and a same pattern shape as that of the structure to be detected, the structure to be detected is at least one of following structures: a gate, a gate scanning line, a data signal line, an active layer, a source, and a drain.

2. The array substrate according to claim 1, wherein a transparent protective layer is disposed above the additional layer.

3. The array substrate according to claim 1, wherein the additional layer is one of a copper layer, an oxide layer of silicon, a nitride layer of silicon, and polyimide layer with addition of a colorant.

4. The array substrate according to claim 1, wherein the additional layer has a thickness of no more than 5000 Å.

5. The array substrate according to claim 1, wherein a transparent protective layer is disposed above the additional layer.

6. The array substrate according to claim 1, wherein the additional layer is one of a copper layer, an oxide layer of silicon, a nitride layer of silicon, and polyimide layer with addition of a colorant.

7. The array substrate according to claim 2, wherein the additional layer is one of a copper layer, an oxide layer of silicon, a nitride layer of silicon, and polyimide layer with addition of a colorant.

8. The array substrate according to claim 1, wherein the additional layer has a thickness of no more than 5000 Å.

9. The array substrate according to claim 2, wherein the additional layer has a thickness of no more than 5000 Å.

10. The array substrate according to claim 3, wherein the additional layer has a thickness of no more than 5000 Å.

11. The array substrate according to claim 2, wherein the transparent protective layer has a thickness of no more than 5000 Å.

12. The array substrate according to claim 7, wherein the transparent protective layer has a thickness of no more than 5000 Å.

13. A detecting method of an array substrate comprising a structure to be detected disposed on a base substrate, wherein an additional layer for detecting whether the structure to be detected is broken is disposed below the structure to be detected, wherein the additional layer has a color different from that of the structure to be detected and a same pattern shape as that of the structure to be detected, the method comprising:
    irradiating white lights on the array substrate formed with the additional layer; and
    determining a color of reflection lights reflected by the array substrate, if the color of the reflection lights having the color of the additional layer, then determining the structure to be detected corresponding to the color of the additional layer having a breakage defect; if the color of the reflection lights having no color of the additional layer, then determining the structure to be detected having no breakage defect, the structure to be detected being at least one of following structures: a gate, a gate scanning line, a data signal line, an active layer, a source, and a drain.

14. The method according to claim 13, wherein at the step of determining the color of the reflection lights, a light filter unit with the same color the additional layer having is disposed in a light path of the reflection lights, and the color of the reflection lights reflected by the array substrate is determined by the lights passing through the light filter unit.

15. A detecting apparatus of an array substrate, the array substrate comprising:
    a structure to be detected disposed on a base substrate, wherein an additional layer for detecting whether the structure to be detected is broken is disposed below the structure to be detected, wherein the additional layer has a color different from that of the structure to be detected and a same pattern shape as that of the structure to be detected, the structure to be detected being at least one of following structures: a gate, a gate scanning line, a data signal line, an active layer, a source, and a drain,
    the detecting apparatus comprising:
    a detecting stage for placing the array substrate to be detected thereon;
    a light source of white color for irradiating white lights on the array substrate formed with the additional layer; and
    a light filter unit for filtering the lights with colors different from the color of the additional layer.

16. The detecting apparatus according to claim 15, wherein the light filter unit is a light filter with the same color as that of the additional layer.

17. The detecting apparatus according to claim 15, further comprising a light detecting unit for identifying the same color as that of the additional layer.

18. The detecting apparatus according to claim 17, further comprising a housing, wherein the light source and the light filter unit are disposed above the detecting stage on opposing sides of the detecting stage respectively, and the light detecting unit is disposed above the light filter unit, and the housing is disposed outside so as to accommodate the detecting stage, the light source, the light filter unit and the light detecting unit.

* * * * *